US011982809B2

(12) United States Patent
Wang

(10) Patent No.: US 11,982,809 B2
(45) Date of Patent: May 14, 2024

(54) ELECTRONIC DEVICE WITH INNER DISPLAY AND EXTERNALLY ACCESSIBLE INPUT-OUTPUT DEVICE

(71) Applicant: Apple Inc., Cupertino, CA (US)

(72) Inventor: Paul X. Wang, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/409,674

(22) Filed: May 10, 2019

(65) Prior Publication Data

US 2020/0088999 A1 Mar. 19, 2020

Related U.S. Application Data

(60) Provisional application No. 62/772,991, filed on Nov. 29, 2018, provisional application No. 62/732,506, filed on Sep. 17, 2018.

(51) Int. Cl.
*G02B 27/01* (2006.01)
*G02B 27/09* (2006.01)
(Continued)

(52) U.S. Cl.
CPC ..... *G02B 27/0172* (2013.01); *G02B 27/0955* (2013.01); *G03B 21/145* (2013.01);
(Continued)

(58) Field of Classification Search
CPC ............ G02B 27/0172; G02B 27/0955; G02B 2027/0156; G02B 27/017; G06F 3/017;
(Continued)

(56) References Cited

U.S. PATENT DOCUMENTS 8,941,560 B2   1/2015 Wong et al.
8,982,471 B1 * 3/2015 Starner ............. G02B 27/0172
                                                       359/13

(Continued)

FOREIGN PATENT DOCUMENTS

CN   102188246 A   9/2011
CN   206193378 U   5/2017

OTHER PUBLICATIONS

Gugenheimer et al., FaceDisplay: Towards Asymmetric Multi-User interaction for Nomadic Virtual Reality, Proceedings of the 2018 CHI Conference on Human Factors in Computing Systems, Paper No. 54, Apr. 21-26, 2018, Montreal QC, Canada.

(Continued)

*Primary Examiner* — Douglas M Wilson
(74) *Attorney, Agent, or Firm* — Treyz Law Group, P.C.; G. Victor Treyz; Kendall P. Woodruff

(57) ABSTRACT

An electronic device may have an inner display mounted in a housing so that an image on the inner display is presented to an eye box through a lens for viewing by a user while the electronic device is being worn on a head of the user. The electronic device may have input-output devices that are operable on external surfaces of the electronic device. The input-output devices may be used to gather user input for controlling an external device while the electronic device is not being worn on the user's head. The input-output devices may include a touch screen display, buttons, and other input-output components. An input-output component may be formed on a movable member that can be moved between a stored position and a deployed position. A projector may project images onto nearby surfaces. A removable electronic device may be coupled to head-mounted support structures or other housing structures.

12 Claims, 8 Drawing Sheets

(51) Int. Cl.

| | | |
|---|---|---|
| *G03B 21/14* | (2006.01) | |
| *G06F 1/16* | (2006.01) | |
| *G06F 1/3231* | (2019.01) | |
| *G06F 3/01* | (2006.01) | |
| *G06F 3/041* | (2006.01) | |
| *H04N 13/344* | (2018.01) | |
| *H04N 13/368* | (2018.01) | |
| *H04N 21/41* | (2011.01) | |

(52) U.S. Cl.
CPC ............ *G06F 3/017* (2013.01); *G06F 3/0412* (2013.01); *G06F 3/0414* (2013.01); *A61M 2205/507* (2013.01); *G02B 27/017* (2013.01); *G06F 1/1649* (2013.01); *G06F 1/3231* (2013.01); *G06F 3/011* (2013.01); *G06F 3/012* (2013.01); *H04N 13/344* (2018.05); *H04N 13/368* (2018.05); *H04N 21/4122* (2013.01)

(58) Field of Classification Search
CPC .... G06F 3/0412; G06F 3/0414; G06F 1/1649; G06F 3/012; G06F 3/011; G06F 1/3231; G03B 21/145; H04N 13/344; H04N 21/4122; H04N 13/368; A61M 2205/507
See application file for complete search history.

(56) References Cited

U.S. PATENT DOCUMENTS

| | | | |
|---|---|---|---|
| 9,046,999 | B1 | 6/2015 | Teller et al. |
| 9,213,185 | B1 | 12/2015 | Starner et al. |
| 9,223,451 | B1 | 12/2015 | Raffle et al. |
| 9,285,592 | B2 | 3/2016 | Olsson et al. |
| 9,341,849 | B2 | 5/2016 | Wong et al. |
| 9,959,678 | B2 | 5/2018 | Katz et al. |
| 10,289,205 | B1 | 5/2019 | Sumter et al. |
| 2008/0013041 | A1 | 1/2008 | Chou |
| 2009/0190046 | A1* | 7/2009 | Kreiner ................ H04N 9/3147 348/789 |
| 2010/0079356 | A1 | 4/2010 | Hoellwarth |
| 2010/0162149 | A1 | 6/2010 | Sheleheda et al. |
| 2011/0169928 | A1 | 7/2011 | Gassel et al. |
| 2011/0194029 | A1 | 8/2011 | Herrmann et al. |
| 2011/0304629 | A1 | 12/2011 | Winchester |
| 2013/0044128 | A1 | 2/2013 | Liu et al. |
| 2013/0117377 | A1 | 5/2013 | Miller |
| 2013/0335321 | A1 | 12/2013 | Sugita et al. |
| 2013/0335573 | A1* | 12/2013 | Forutanpour ............ G06F 3/011 345/173 |
| 2014/0062854 | A1* | 3/2014 | Cho .................. G06F 3/016 345/156 |
| 2014/0111864 | A1* | 4/2014 | Margulis ............ G02B 27/0172 359/630 |
| 2014/0160250 | A1 | 6/2014 | Pomerantz et al. |
| 2014/0361977 | A1 | 12/2014 | Stafford et al. |
| 2014/0368537 | A1 | 12/2014 | Salter et al. |
| 2015/0002465 | A1 | 1/2015 | Tsukahara et al. |
| 2015/0067580 | A1 | 3/2015 | Um et al. |
| 2015/0253573 | A1 | 9/2015 | Sako et al. |
| 2015/0379896 | A1 | 12/2015 | Yang et al. |
| 2016/0018655 | A1 | 1/2016 | Imoto et al. |
| 2016/0041396 | A1 | 2/2016 | Kawamura et al. |
| 2016/0216792 | A1 | 7/2016 | Ogawa et al. |
| 2016/0224176 | A1 | 8/2016 | Kim et al. |
| 2016/0357318 | A1 | 12/2016 | Chan et al. |
| 2017/0068500 | A1* | 3/2017 | Rochford ................ G06F 3/011 |
| 2017/0206688 | A1 | 7/2017 | Chun et al. |
| 2017/0230640 | A1 | 8/2017 | Rochford et al. |
| 2017/0255019 | A1* | 9/2017 | Lyons ..................... G06F 3/011 |
| 2018/0003983 | A1* | 1/2018 | Sako .................... H04N 13/344 |
| 2018/0004478 | A1 | 1/2018 | Chen |
| 2018/0024799 | A1* | 1/2018 | Jarvenpaa ............... G06F 3/011 345/156 |
| 2018/0046147 | A1 | 2/2018 | Aghara et al. |
| 2018/0096533 | A1 | 4/2018 | Osman |
| 2018/0101227 | A1 | 4/2018 | Frueh et al. |
| 2018/0184974 | A1 | 7/2018 | Cimenser et al. |
| 2018/0314323 | A1 | 11/2018 | Mikhailov et al. |
| 2018/0368559 | A1 | 12/2018 | Wang et al. |
| 2018/0373371 | A1 | 12/2018 | Kim |
| 2019/0101977 | A1 | 4/2019 | Armstrong-Muntner et al. |
| 2019/0129181 | A1 | 5/2019 | Polcak et al. |
| 2019/0243598 | A1* | 8/2019 | Kim .......................... G06T 1/20 |
| 2019/0265781 | A1* | 8/2019 | Kehoe ..................... G06F 1/163 |
| 2020/0310121 | A1 | 10/2020 | Choi et al. |
| 2021/0042979 | A1 | 2/2021 | Ballagas et al. |

OTHER PUBLICATIONS

Mai et al., Transparent HMD: Revealing the HMD User's Face to Bystanders, MUM 2017, Nov. 26-29, 2017, Stuttgart, Germany.

Pohl et al. See what I See: concepts to improve the social acceptance of HMDs, 2016 IEEE Virtual Reality (VR), Mar. 19-23, 2016, Greenville, SC, USA.

Misawa et al., Wearing Another's Personality: A Human-Surrogate System with a Telepresence Face, ISWC '15, Sep. 7-11, 2015, 8 pages, Osaka, Japan.

Osawa et al., Emotional Cyborg: Human Extension with Agency for Emotional Labor, HRI '14, Mar. 3-6, 2014, 1 page, Bielefed, Germany.

Qiu et al., E-Gazes Glasses: Simulating Natural Gazes for Blind People, TEI '16, Feb. 14-17, 2016, 8 pages, Eindhoven, Netherlands.

Ens et al., Candid Interaction: Revealing Hidden Mobile and Wearable Computing Activities, UIST '15, Nov. 8-11, 2015, 10 pages, Charlotte, NC, USA.

Falk et al., The BubbleBadge: A Wearable Public Display, PLAY: Applied Research on Art and Technology, May 29, 2014, 3 pages, Gothenburg, Sweden.

Chan et al., FrontFace: Facilitating Communication Between HMD Users and Outsiders Using Front-Facing Screen HMDs, MobileHCI '17, Sep. 4-7, 2017, 5 pages, Vienna, Austria.

Gugenheimer et al., FaceDisplay: Enabling Multi-User Interaction for Mobile Virtual Reality, CHI '17, May 6-11, 2017, 4 pages, Denver, CO, USA.

Frueh et al., Headset Removal for Virtual and Mixed Reality, SIGGRAPH '17 Talks, Apr. 1, 2017, 2 pages, Los Angeles, CA, USA.

\* cited by examiner

ELECTRONIC DEVICE WITH INNER DISPLAY AND EXTERNALLY ACCESSIBLE INPUT-OUTPUT DEVICE

This application claims the benefit of provisional patent application No. 62/732,506, filed Sep. 17, 2018, and provisional patent application No. 62/772,991, filed Nov. 29, 2018, which are hereby incorporated by reference herein their entireties.

FIELD

This relates generally to electronic devices, and, more particularly, to electronic devices with displays.

BACKGROUND

Electronic devices often include displays. Wearable electronic devices such as head-mounted devices have displays for presenting images to users while the devices are being worn.

In some situations, it can be challenging for a user to interact with an electronic device such as a head-mounted electronic device. When a head-mounted electronic device is being worn by a user, the user can view content on the display of the head-mounted device. In this mode of operation, selectable on-screen options may be presented on the display with which the user may interact to supply input to the device. When the head-mounted electronic device is not being worn, however, the user cannot view content on the display, which hinders the ability of the user to interact with the device and associated equipment.

SUMMARY

An electronic device such as a head-mounted device may have an inner display mounted in a housing. The housing may have head-mounted support structures configured to support the inner display and to support associated lenses adjacent to a user's head. The inner display may output light that passes through lenses to eye boxes. When the eyes of the user are located in the eye boxes, the user may view images being presented on the inner display.

The electronic device may have input-output devices that are accessible on external surfaces of the electronic device. The input-output devices may include, for example, buttons, keys in a keyboard, touch sensors such as touch sensors overlapping displays, and other input-output devices.

The input-output devices of the electronic device may be used to gather user input from the user when the electronic device is not being worn on the user's head. For example, the input-output devices may gather user input when the electronic device is being held in a user's hand or is resting on a table top.

The head-mounted device may communicate with associated external electronic equipment such as a computer, gaming system, cellular telephone, or other host. In some configurations, the head-mounted device may serve as a stand-alone device.

During operation of the head-mounted device while the head-mounted device is not being worn on the head of the user and the inner display is not presenting images that are viewed by the user, the user may supply user input for controlling the head-mounted device and/or for controlling the external electronic equipment. The head-mounted device may communicate with the external electronic equipment wirelessly, so that the user input can be used in controlling the external electronic equipment.

In some configurations, an input-output component may be formed on a movable member that can be moved between a stored position and a deployed position. A projector may project images onto nearby surfaces. The images may include a virtual keyboard with which a user may interact. If desired, a removable electronic device may be coupled to head-mounted support structures or other housing structures in the head-mounted device.

DETAILED DESCRIPTION

An electronic device such as a head-mounted device may be provided with head-mounted support structures that allow the electronic device to be worn on a user's head. While being worn on the user's head, a display in the electronic device may present an image for viewing by the user. During on-head operations, the user may interact with the device using a controller or controls on the device. For example, the user may view and select on-screen options that are displayed on the display using one or more remote controls such as wireless handheld controllers.

When the user removes the electronic device from the user's head, the user may still interact with the electronic device by using input-output components that are accessible while the electronic device is not being worn and while the image on the display is not being viewed by the user. The external input-output components may include buttons, touch screen displays, projectors, and other input-output circuitry. Components such as these may be mounted on external device surfaces that are accessible when the electronic device is resting on a table top or is otherwise not being worn on the user's head. In some configurations, the external input-output components can also be used by the user or by others while the electronic device is being worn by the user. For example, an external display on the electronic device may present content that is viewed by others while the user is viewing content with an internal user-viewable display. The electronic device may be a stand-alone head-mounted device and/or may be a head-mounted device that interacts with external electronic equipment.

Figure 1:
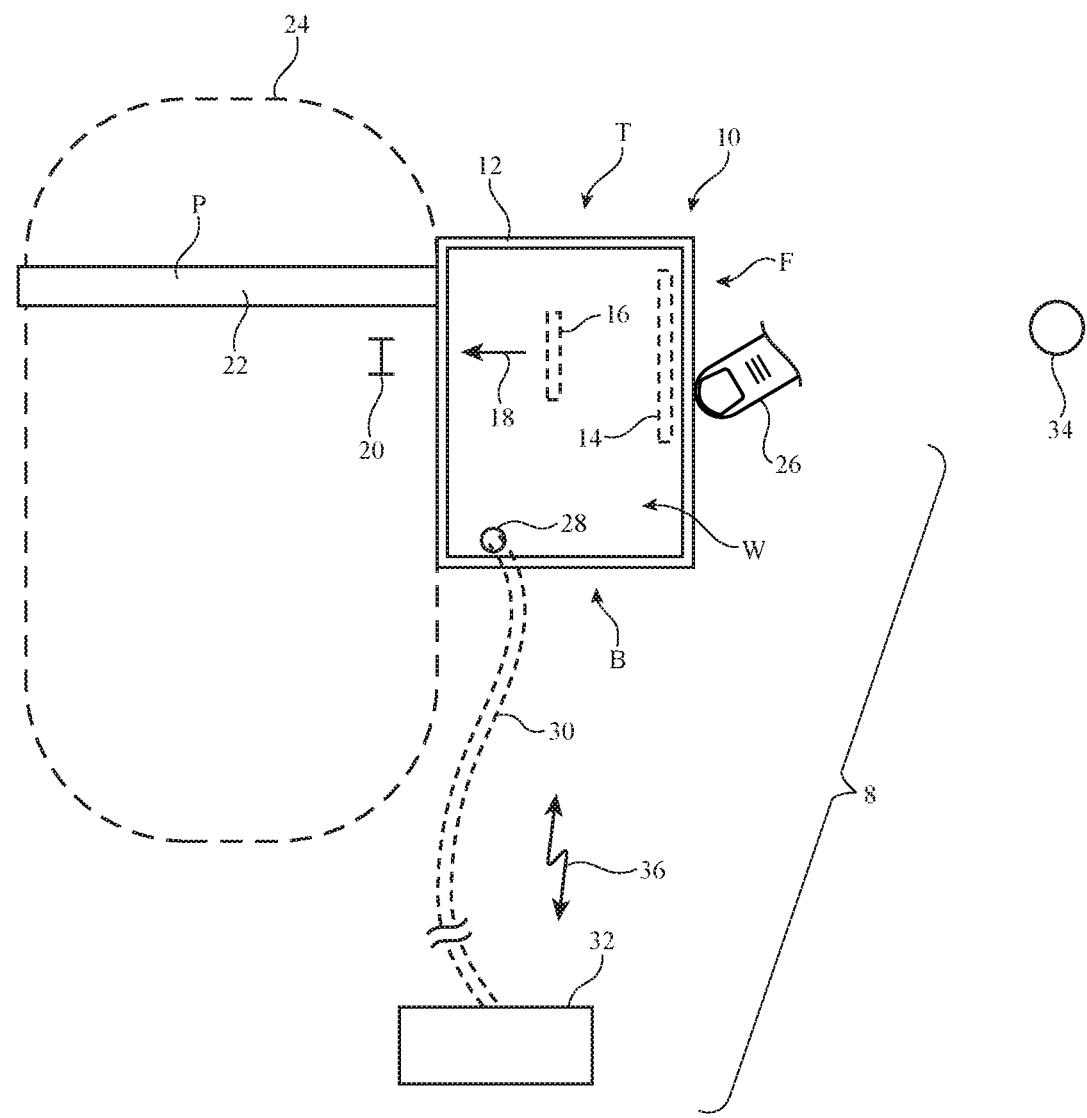
FIG. 1 is a schematic diagram of an illustrative system that includes an electronic device such as a head-mounted device and optional external electronic equipment in accordance with an embodiment.

An illustrative system of the type that may include an electronic device with external input-output components is shown in FIG. 1. As shown in FIG. 1, system 8 may include electronic device such as electronic device 10 and optional external electronic equipment 32. In an illustrative configuration, electronic device 10 is a head-mounted (head-mountable) electronic device. In general, device 10 and/or external electronic equipment 32 may be any suitable electronic equipment. For example, device 10 and/or equipment 32 may be devices such as a laptop computer, a computer monitor containing an embedded computer (e.g., a desktop computer formed from a display with a desktop stand that has computer components embedded in the same housing as the display), a tablet computer, a cellular telephone, a media player, or other handheld or portable electronic device, a smaller device such as a wrist-watch device, a pendant device, a headphone or earpiece device, a device embedded in eyeglasses or other equipment worn on a user's head, or other wearable or miniature device, a television, a computer display that does not contain an embedded computer, a gaming device (e.g., a game console such as a set-top box or other game system), a navigation device, a tower computer, an embedded system such as a system in which electronic equipment with a display is mounted in a kiosk or automobile, equipment that implements the functionality of two or more of these devices, or other electronic equipment.

As shown in FIG. 1, electronic device 10 may have a housing such as housing 12. Housing 12 may have portions that are configured to allow device 10 to be worn on a user's head 24. For example, housing 12 may have the shape of a pair of eyeglass, a helmet, goggles, a hat, etc. and may include or be coupled to a housing structure such as a strap, eyeglass temples, helmet support structure, googles frame, and/or other head-mounted support structures such as head-mounted support structure 22. Support structure 22 may be attached to the main body portion of housing 12 using a fixed connection or a removable connection.

Housing 12 and associated support structure 22 may be formed from metal, polymer, glass, ceramic, crystalline material such as sapphire, soft materials such as fabric and foam, wood or other natural materials, other materials, and/or combinations of these materials. Housing 12 may be configured to form a housing for eyeglasses, goggles, a helmet, a hat, a visor, and/or other head-mounted electronic device.

Display 14 may be mounted in housing 12. During operation, display 14 may display an image that is viewable by a user through lenses such as lens 16. Display 14 may contain a single pixel array that spans left and right lenses and/or may have separate left and right portions associated respectively with left and right lenses. Light from display 14 is directed through the lenses in direction 18 toward left and right eye boxes 20. When electronic device 10 is being worn on user's head 24, the eyes of the user will be located in eye boxes 20 and the image on display 14 can be viewed by the user. If desired, left and right portions of display 14 may be mounted in movable left and right lens modules each of which includes a corresponding lens 16. The positions of these lens module structures may, if desired, be adjusted to help focus the display image and/or to accommodate a user's head (e.g., to accommodate a user's interpupillary distance).

In some configurations, an optical coupler may be incorporated into housing 12 so that the user may view real-world objects such as object 34 while computer-generated content on display 14 is overlaid over object 34. Device 10 may also include a camera that captures images of object 34 in real time, so that computer-generated content and/or captured images of real-world objects can be displayed together for the user without using an optical coupling arrangement. In other configurations, housing 12 is opaque and device 10 is configured to display only computer-generated content on display 14 for the user.

Device 10 may have exterior surfaces that are planar, that have a curved cross-sectional profile, and/or that have other suitable shapes. In the example of FIG. 1, housing 12 has planar and/or curved surfaces on upper side T, front side F, left and right sides W, and lower side B. The exposed external surfaces on sides P of head-mounted support structure 22 may be planar and/or may be curved. In general, any suitable electronic components in device 10 may be mounted on one or more sides of device 10. As an example, one or more externally accessible input-output devices (touch sensitive and/or touch insensitive displays, force sensitive and/or force-insensitive displays, displays that include overlapping touch and force sensors and that are therefore sensitive to both force and touch input, buttons, sensors, etc.) may be located on one or more of sides T, F, W, B, and/or P of device 10. Proximity sensors (e.g., image sensors or other optical sensors, capacitive proximity sensors, and/or other proximity sensors) may be incorporated into one or more of sides T, F, W, B, and/or P to gather hovering input (sometimes referred to as non-contact input or air gestures). The non-contact input may include input gathered while a user's finger is 1-300 mm, at least 0.5 mm, at least 5 mm, at least 50 mm, less than 500 mm, or other suitable distance from device 10 (e.g., the side of device 10 on which the proximity sensor is located) and while the finger is not touching device 10. These input-output devices may be used by a user while wearing device 10, may be used by a user while not wearing device 10 (e.g., while device 10 is resting on a table or other support structure and while display 14 is optionally off) and/or may be used by others while the user is wearing or is not wearing device 10. As an example, a user may supply touch input, force input, non-contact input to a proximity sensor, or other input using one or more external objects such as fingers 26 (e.g., finger 26 may supply touch input to a touch sensor overlapping a display or other device on an exterior surface of device 10). If desired, input may also be provided by motions of a user's hands (e.g., air gestures involving hand swiping through the air without touching device 10), and/or input from other user body parts (e.g., portions of a user's body other than fingers and/or including fingers and other body parts). The external objects may include accessories such as a stylus (electronic pencil) with internal control circuitry and communications circuitry, a circuitry-free stylus, a finger-mounted device (e.g., a device that clips to a user's finger and that contains control and communications circuitry and/or input-output circuitry such as sensors and haptic output circuitry), a joystick or other handheld wireless controller, and/or other input-output device.

In some configurations, a finger or other external object may directly contact and press against a display or other input device that is force sensitive and/or touch sensitive to supply that input device with input. An external object such as an electronic accessory may also have an inertial measurement unit and/or other sensor circuitry that tracks the location of the accessory and/or that gathers other input and may convey this information to device 10 in real time (e.g., using wireless communications circuitry or other communications circuitry).

If desired, device 10 may interact with an accessory, finger, or other external object to monitor the location and movement of that object and thereby gather user input. As an example, a sensor 50 in device 10 may track the location (and therefore the movement) of objects using light-based tracking systems (e.g., cameras, three-dimensional image sensors or other depth sensors), radio-frequency tracking systems, acoustic tracking systems, or other tracking systems and/or may receive location input and other input from circuitry in an accessory. By tracking the position of a finger, finger-mounted device, stylus, wireless controller, and/or other external object and/or by gathering other information on the behavior of the external object, device 10 may gather input such as user input with or without measuring direct force and/or touch input on the surfaces of device 10.

In some configurations, device 10 may be a stand-alone device. In other situations, device 10 may be coupled to external equipment 32 using a wired or wireless link. As shown in FIG. 1, for example, device 10 may have a wired port such as port 28 to which a cable such as cable 30 may be coupled. Using a wired communications path such as cable 30, a wired link may be formed between device 10 and external electronic equipment 32. If desired, wireless communications circuitry may be provided in device 10 and equipment 32 to support communications between device 10 and equipment 32 over wireless communications link 36.

There may, in general, be any suitable number of external devices (equipment 32) in system 8. For example, device 10 may be a stand-alone device that operates with one or more accessory devices such as wireless controllers. As another example, device 10 may serve as an input-output accessory that interacts with a host computing device (e.g., device 10 can provide user input to equipment 32 for controlling equipment 32 and equipment 32 can optionally receive additional input from wireless controllers or other devices in system 10). During operation, a host device may supply content to device 10 for displaying to a user and/or others. The user may interact with the system by supplying input (and receiving output) using device 10 and/or using optional additional input-output devices such as wireless controllers.

Figure 2:
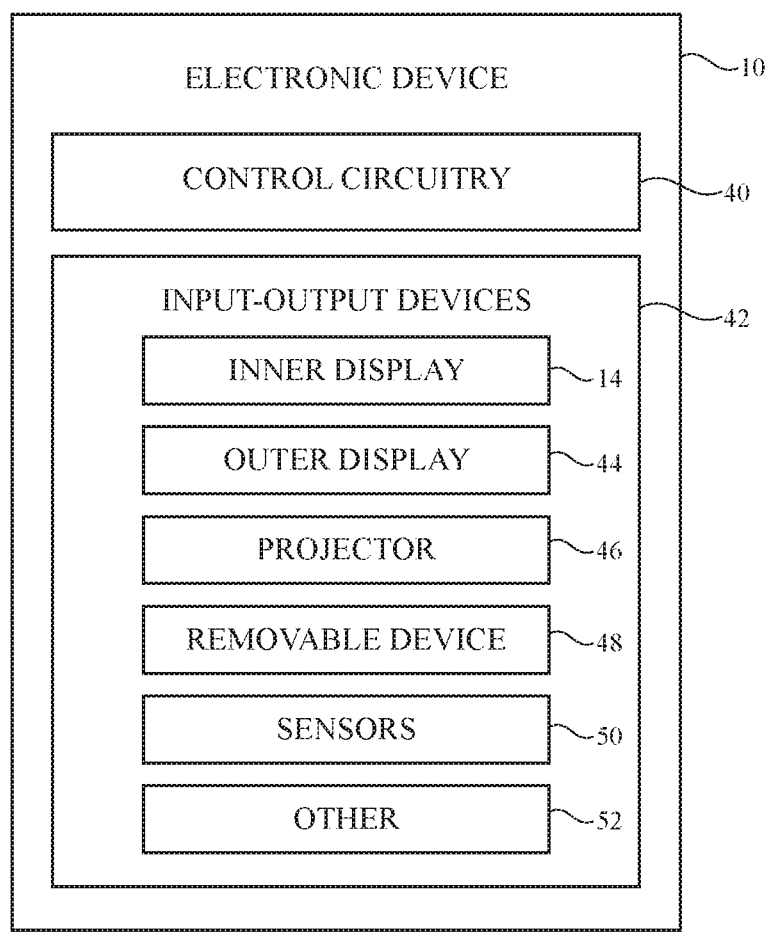
FIG. 2 is a schematic diagram of an illustrative electronic device in accordance with an embodiment.

FIG. 2 is a schematic diagram of an illustrative electronic device for system 8. As shown in FIG. 2, electronic device 10 may have control circuitry 40. Control circuitry 40 may include storage and processing circuitry for supporting the operation of device 10. The storage and processing circuitry may include storage such as hard disk drive storage, non-volatile memory (e.g., flash memory or other electrically-programmable-read-only memory configured to form a solid state drive), volatile memory (e.g., static or dynamic random-access-memory), etc. Processing circuitry in control circuitry 40 may be used to control the operation of device 10. The processing circuitry may be based on one or more microprocessors, microcontrollers, digital signal processors, baseband processors, power management units, audio chips, application specific integrated circuits, etc. Control circuitry 40 may include wired and/or wireless communications circuitry (e.g., antennas and associated radio-frequency transceiver circuitry such as cellular telephone communications circuitry, wireless local area network communications circuitry, etc.). The communications circuitry of control circuitry 40 may allow device 10 to communicate with keyboards, computer mice, remote controls, wireless handheld controllers with accelerometers or other sensors, speakers, accessory displays, accessory cameras, and/or other electronic devices that serve as accessories for device 10 and/or may allow device 10 to communicate with computers, gaming systems, cellular telephones, and/or other external devices (e.g., host devices), as shown by wireless link 36 and external electronic equipment 32 of FIG. 1.

Input-output circuitry in device 10 such as input-output devices 42 may be used to allow data to be supplied to device 10 and to allow data to be provided from device 10 to external devices. Input-output devices 42 may include input devices that gather user input and other input and may include output devices that supply visual output, audible output, or other output. These devices may include buttons, joysticks, scrolling wheels, touch pads (e.g., capacitive touch sensors and/or other touch sensors), key pads, keyboards, microphones, speakers, tone generators, vibrators and other haptic output devices, light-emitting diodes and other status indicators, etc.

Input-output devices 42 may include one or more displays such as inner display 14 (see, e.g., FIG. 1). One or more externally viewable displays such as outer display 44 may also be included in device 10. Display 14 and/or display 44 may, for example, be displays such as an organic light-emitting diode display with an array of thin-film organic light-emitting diode pixels, a liquid crystal display with an array of liquid crystal display pixels and an optional backlight unit, a display having an array of pixels formed from respective crystalline light-emitting diodes each of which has a respective crystalline semiconductor light-emitting diode die, and/or other displays. In some configurations, input-output devices 42 may include a projector display such as project 46 based on a micromechanical systems device such as a digital micromirror device or other projector components. Projector 46 may project images onto nearby surfaces. Display 44 and/or projector 46 may be mounted on exterior surfaces of device 10 (e.g., on sides T, F, W, B, and/or P of FIG. 1). Because outer display 44 is accessible from the exterior of device 10, display 44 may sometimes be referred to as an externally viewable or publically viewable display. With one illustrative configuration, display 44 may have a portion that is mounted on front side F or other forward-facing portion of device 10 so that display 44 may be viewed by people in the vicinity of device 10 when device 10 is being worn by a user.

Display 44 may be a touch screen display that includes a touch sensor for gathering touch input from a user or display 44 may be a touch insensitive display that is not sensitive to touch. A touch sensor for display 44 may be based on an array of capacitive touch sensor electrodes, acoustic touch sensor structures, resistive touch components, force-based touch sensor structures, a light-based touch sensor, or other suitable touch sensor arrangements.

Input-output devices 42 may include sensors 50. Sensors 50 may be mounted on external surfaces of device 10, may operate through windows or other portions of the housing for device 10, and/or may be mounted in one or more interior regions of device 10.

Sensors 50 may include force sensors (e.g., strain gauges, capacitive force sensors, resistive force sensors, etc.), audio sensors such as microphones, touch and/or proximity sensors such as capacitive sensors (e.g., a two-dimensional capacitive touch sensor integrated into outer display 44, a two-dimensional capacitive touch sensor overlapping display 44, and/or a touch sensor that forms a button, trackpad or other two-dimensional touch sensor, or other input device not associated with a display), and other sensors. If desired, sensors 50 may include optical sensors such as optical sensors that emit and detect light, ultrasonic sensors, optical touch sensors, optical proximity sensors, and/or other touch sensors and/or proximity sensors, monochromatic and color ambient light sensors, image sensors, fingerprint sensors, temperature sensors, capacitive sensors, image sensors, or other sensors for measuring three-dimensional non-contact gestures ("air gestures", sometimes referred to as hovering gestures), pressure sensors, sensors for detecting position, orientation, and/or motion (e.g., accelerometers, magnetic sensors such as compass sensors, gyroscopes, and/or inertial measurement units that contain some or all of these sensors), health sensors, radio-frequency sensors (e.g., sensors that gather position information, three-dimensional radio-frequency images, and/or other information using radar principals or other radio-frequency sensing), depth sensors (e.g., structured light sensors and/or depth sensors based on stereo imaging devices), optical sensors such as self-mixing sensors and light detection and ranging (lidar) sensors that gather time-of-flight measurements, humidity sensors, moisture sensors, gaze tracking sensors, three-dimensional sensors (e.g., pairs of two-dimensional image sensors that gather three-dimensional images using binocular vision, three-dimensional structured light sensors that emit an array of infrared light beams or other structured light using arrays of lasers or other light emitters and associated optical components and that capture images of the spots created as the beams illuminate target objects, and/or other three-dimensional image sensors), facial recognition sensors based on three-dimensional image sensors, visual odometry sensors based on image sensors, and/or other sensors. In some arrangements, device 10 may use sensors 50 and/or other input-output devices to gather user input (e.g., buttons may be used to gather button press input, touch sensors overlapping displays can be used for gathering user touch screen input, touch pads may be used in gathering touch input, microphones may be used for gathering audio input, etc.).

If desired, electronic device 10 may include additional components 52. Components 52 may include haptic output devices, audio output devices such as speakers, light sources such as light-emitting diodes (e.g., crystalline semiconductor light-emitting diodes for status indicators and/or components), other optical output devices, and/or other circuitry for gathering input and/or providing output. Device 10 may also include an optional battery or other energy storage device, connector ports such as port 28 of FIG. 1 for supporting wired communications with ancillary equipment and for receiving wired power, and other circuitry.

Figure 3:
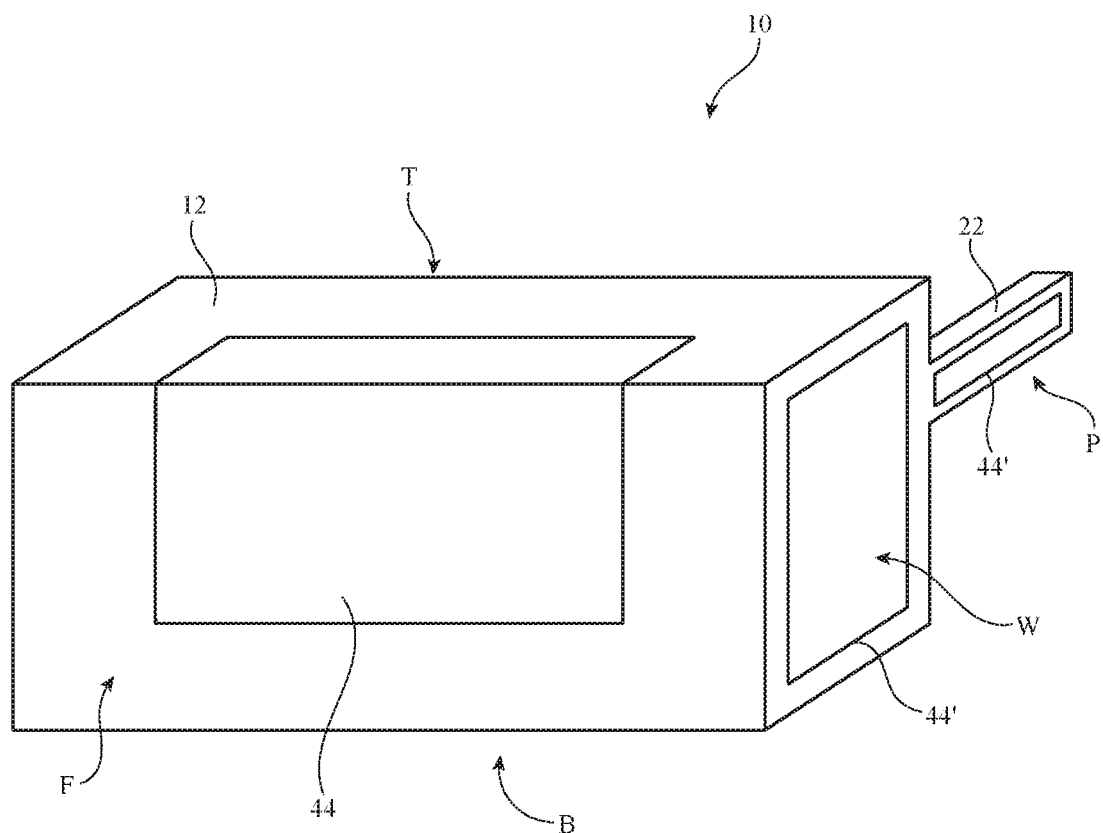
FIG. 3 is a perspective view of an illustrative electronic device in accordance with an embodiment.

FIG. 3 is a perspective view of device 10 in an illustrative configuration in which outer display 44 is formed on exterior portions of device 10 (e.g., on top side T and front side F). As shown by illustrative additional outer display locations 44', outer displays such as outer display 44 may be mounted on any exterior surface of device 10 including exterior portions of head-mounted support structure 22 and/or the main body portion of housing 12 (e.g., outer displays 44 may be formed on one or more of sides T, B, F, W, and/or P). Each externally viewable display may cover a single side of device 10 and/or portions of two or more sides as shown by display 44 in the example of FIG. 3.

When device 10 is not being worn on a user's head, device 10 may be supported on a table top or other support structure and/or may be held in the hand. In this type of scenario, device 10 and the sensors and other input-output devices 42 of device 10 allow device 10 to be used at an accessory controller for external electrical equipment 32. For example, if a user desires to use an online service, the user may interact with keyboard keys and/or on-screen keys on display 44 to provide the online service with text and other information, to supply the online service with commands (e.g., by selecting on-screen options), and/or by otherwise providing the service with input using the input circuitry of device 10. Corresponding output from the service may be provided to the user using the output circuitry of device 10 (e.g., audio output, visual output, haptic output, etc.). Because device 10 does not need to be placed over the eyes of the user while the user supplies input and receives output from device 10, the user may stay engaged with people in the vicinity of the user, may remain aware of the user's surroundings, and/or the ability of the user to interact with system 8 may otherwise be enhanced. If desired, a user may provide device 10 with input in this way (e.g., while device 10 is being held in a user's hand) when device 10 is being used as a stand-alone device.

If desired, display 44 may mirror some or all of the content being displayed on display 14 (e.g., while device 10 is being worn by the user) and/or may be used by control circuitry 40 to display content that is associated with the content being displayed on display 14. For example, if display 14 is being used to present a game to a user who is wearing device 10, display 44 may display some or all of the same game images that are being displayed for the user on display 14 to people in the vicinity of the user. Game statistics such as game scores, text that informs others that the user is playing the game (e.g., "game in progress"), and/or other suitable information related to the content on display 14 may also be displayed on outer display 44.

Figure 4:
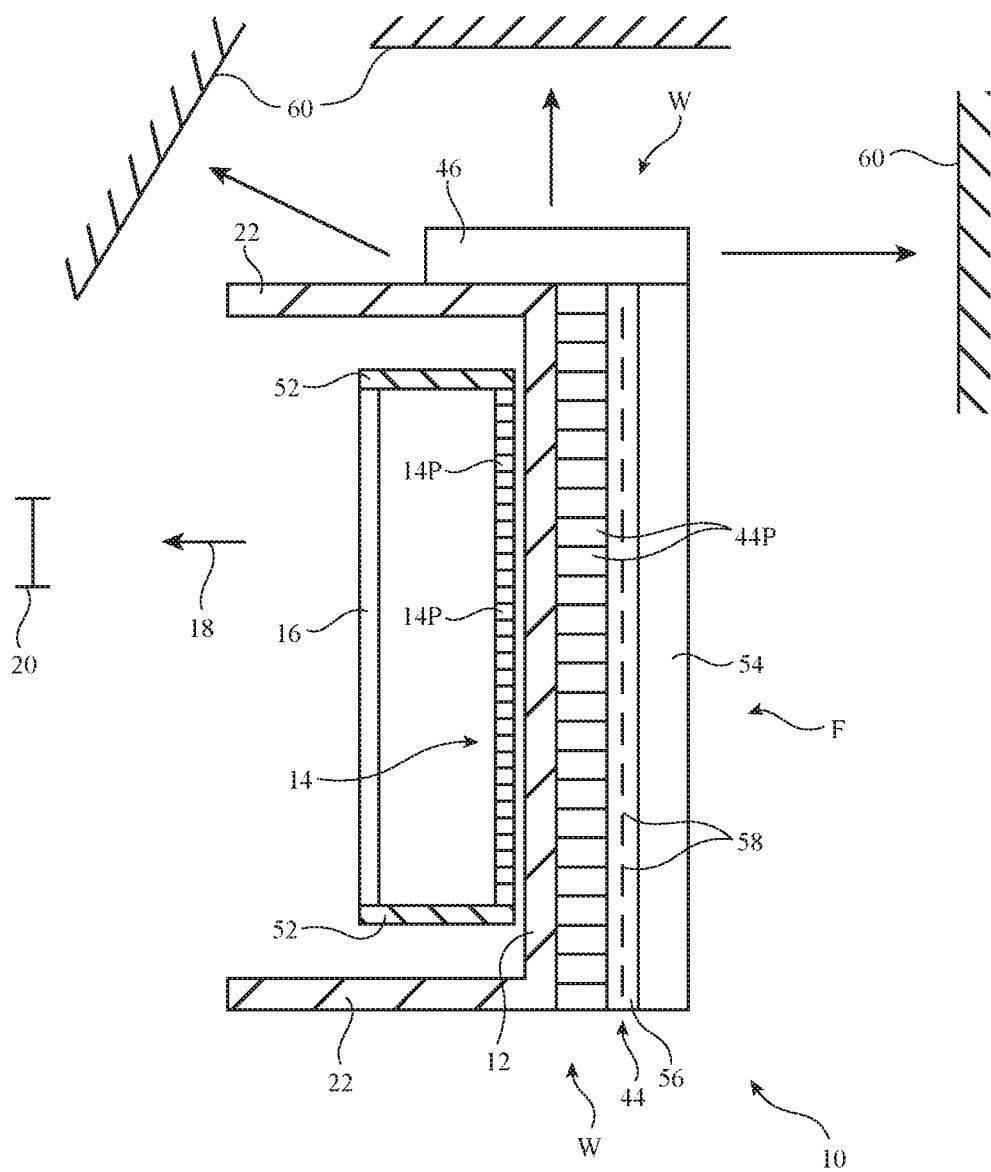
FIG. 4 is a cross-sectional side view of an illustrative electronic device in accordance with an embodiment.

FIG. 4 is a cross-sectional side view of device 10 in an illustrative configuration in which device 10 includes projector 46. Inner display 14 may have an array of pixels 14P. Display 14 emits light in direction 18 through lenses such as lens 16. This allows a user whose eyes are located in eye boxes 20 to view images on display 14. If desired, each lens 16 and a respective portion of inner display 14 may be mounted in a lens module using lens module structures 52 (e.g., support structures formed from polymer, metal, and/or other material). There may separate left and right lens modules for the user's left and right eyes, respectively. Structures 52 may be coupled to housing 12. If desired, electrically adjustable actuators controlled by control circuitry 40 may be used in moving the lens modules within housing 12.

Outer display 44 may be mounted on front side F of device 10 (as an example). Outer display 44 may have an array of pixels 44P. Touch sensor structures may be incorporated into pixels 44P and/or a two-dimensional capacitive touch sensor or other touch sensor may overlap pixels 44P. In the example of FIG. 4, two-dimensional capacitive touch sensor 56 has been coupled over the front of display 44 (e.g., display 44 is a touch sensitive display). Touch sensor 56 may have one or more transparent polymer layers or other transparent layers on which an array of transparent conductive electrodes 58 (e.g., an array of indium tin oxide electrodes) is formed (as an example). A layer of adhesive may be used in attaching touch sensor 56 to the outer surface of outer display 44. Optional display cover layer 54 (e.g., a transparent layer of polymer or glass) may be mounted over touch sensor 56.

As shown in FIG. 4, projector 46 may project one or more images onto adjacent surfaces 60 during operation of device 10. The information provided by projector 46 may be the same as the information displayed on display 14 (e.g., the displayed information from projector 46 may be a game image for a game being displayed on display 14), may be associated with the information displayed on display 14 (e.g., game statistics), may be information about the user of device 10 and/or the status of device 10 (e.g., "game in progress"), may be any other suitable information related to the operation of display 14 and/or device 10, or other information.

Figure 5:
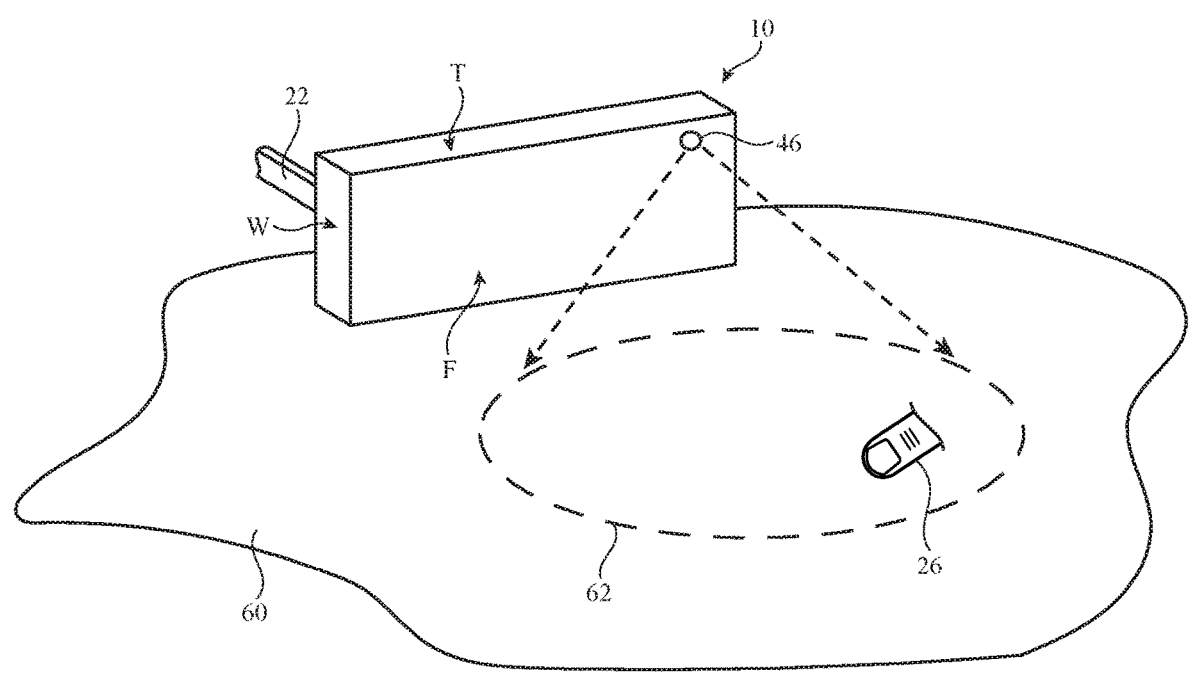
FIG. 5 is perspective view of an illustrative electronic device resting on a surface in accordance with an embodiment.

FIG. 5 is a diagram of device 10 in an illustrative scenario in which device 10 is resting on a table top or other external surface such as surface 60. Projector 46 in device 10 may display images such as image 62 on surface 60. The content of image 62 may be the same content that would have been displayed on display 14 if device 10 were being worn on the head of the user and/or may be any other suitable information. As an example, a user may use a web browser application that is running on device 10 to obtain information from the internet while this information is being presented to the user as part of image 62.

If desired, a sensor (e.g. a three-dimensional image sensor or other sensor in device 10) may sense finger input at various portions of image 62 from a user's finger (finger 26). This allows the user to interact with the content being displayed on surface 60. For example, device 10 may display a selectable option that is associated with an online service or an application running on device 10 in image 62. The user may place finger 26 on that selectable option (e.g., using a single tap, double tap, or other suitable user input). In response to detecting the user finger input corresponding to the selectable option (e.g., by analyzing data from the three-dimensional sensor), device 10 can conclude that the user has selected the selectable option and can initiate an operation in device 10 that is associated with the selectable option. Device 10 may, for example, retrieve and display additional online content, can adjust an electrical component in device 10, etc. If desired, projector 46 may project a virtual keyboard onto surface 60 and the three-dimensional sensor or other suitable sensor in device 10 may gather virtual keyboard input from the user as the user types on alphanumeric labels on virtual keys in the virtual keyboard.

In general, device 10 may include any suitable circuitry for tracking the location of external objects such as finger 26. This circuitry may include sensors 50 in device 10 (e.g., light-based tracking circuitry such as cameras, three-dimensional image sensors and other depthsensors, radio-frequency tracking circuitry, acoustic tracking circuitry, capacitive sensors for sensing touch input and hovering gestures, other sensors 50, etc.) and/or may include circuitry in an external object (e.g., sensors such sensors 50 that are located in an electronic pencil or other external electronic device and that interact with control circuitry such as control circuitry 40 that is located in the external electronic device). The external object(s) being tracked in this way may include a user's finger or items with circuitry that can optionally be used in gathering input. The external objects may include, for example, a stylus (e.g., a wireless electronic pencil), a finger-mounted device, a remote control, joystick, or other controller (e.g., a game controller), and/or other external items. In scenarios in which an external object has sensors for gathering input, this input may be provided to device 10 (e.g., by wirelessly communicating the input to device 10 in real time).

Figure 6:
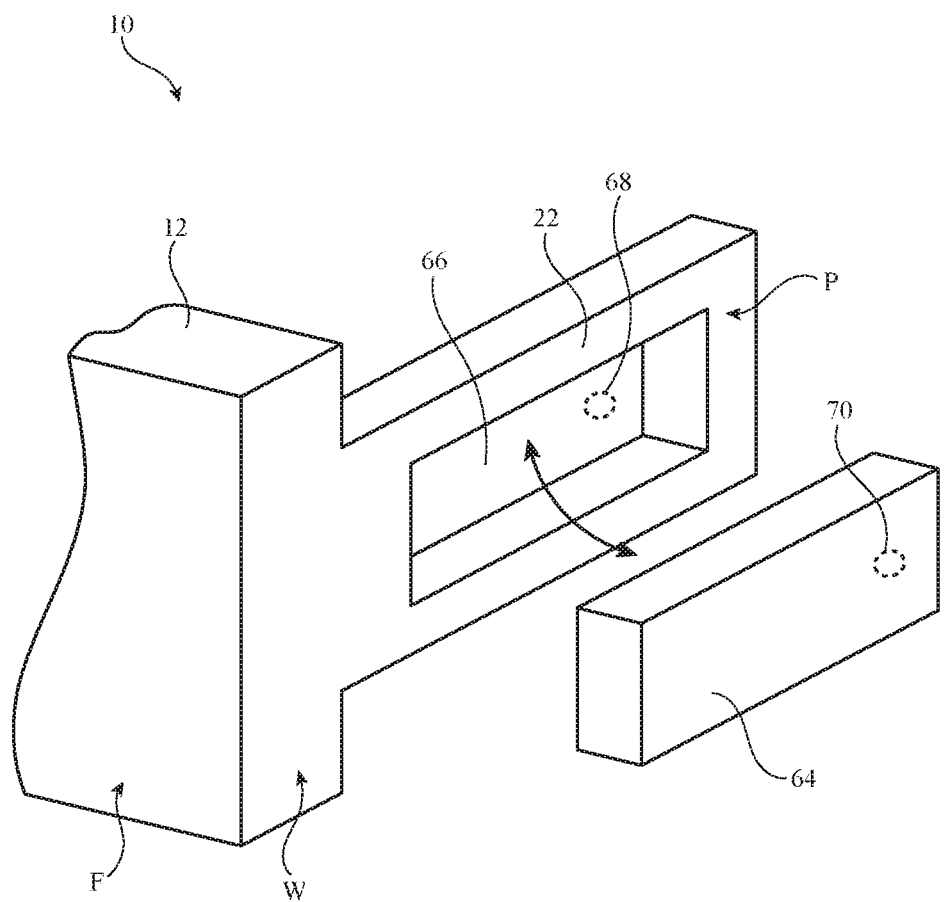
FIG. 6 is a perspective view of a portion of an electronic device that is configured to store a removable electronic device in accordance with an embodiment.

User input may be supplied by moving a user's finger(s), by moving finger-mounted devices, by moving electronic pencils, by moving controllers, by supplying air gestures, and/or by otherwise using these items in supplying input (e.g., touch input, button input, joystick input, touch and/or force sensor input, optical input, and/or other input). User input may be gathered, for example, as a sensor in device 10 tracks the location of an external object in a location that overlaps image 62 of FIG. 5 and/or as circuitry in a stylus or other external object gathers the user input (as examples). If desired, a user may use a stylus, finger-mounted device, or other electronic device (e.g., an accessory) or a fingertip to move virtual objects or to otherwise interact with visual content in image 62. A user may trace out paths on surface 60 with a pencil or other electronic accessory or with a fingertip. Device 10 may use sensor circuitry in device 10 and/or in an external device to detect the paths that are traced out and may dynamically present corresponding computer-generated lines that follow the paths and/or other computer-generated content within image 62 on surface 60. FIG. 6 is a perspective view of a portion of device 10 in an illustrative arrangement in which device 10 has been configured to store a removable handheld device such as handheld (portable) device 64. Device 64 may be a wireless stylus, a wireless remote control, an accelerometer-based wireless controller, and/or other electronic device. As shown in FIG. 6, head-mounted support structures 22 or other portions of housing 12 may be provided with structures that facilitate temporary coupling of device 64 to device 10. For example, recess 66 may be formed on side P of support structures 22. Magnetic structures 68 may be provided in device 10 that mate with corresponding magnetic structures 70 in device 64. Structures 68 and 70 may include permanent magnets and/or magnetic material (e.g., iron bars) so that structures 68 and 70 attract each other when device 64 is placed within recess 66. This holds device 64 in place (e.g., so that device 64 can be stored in device 10, so that wired and/or wireless power can be transferred between device 10 and device 64, etc.).

Figure 7:
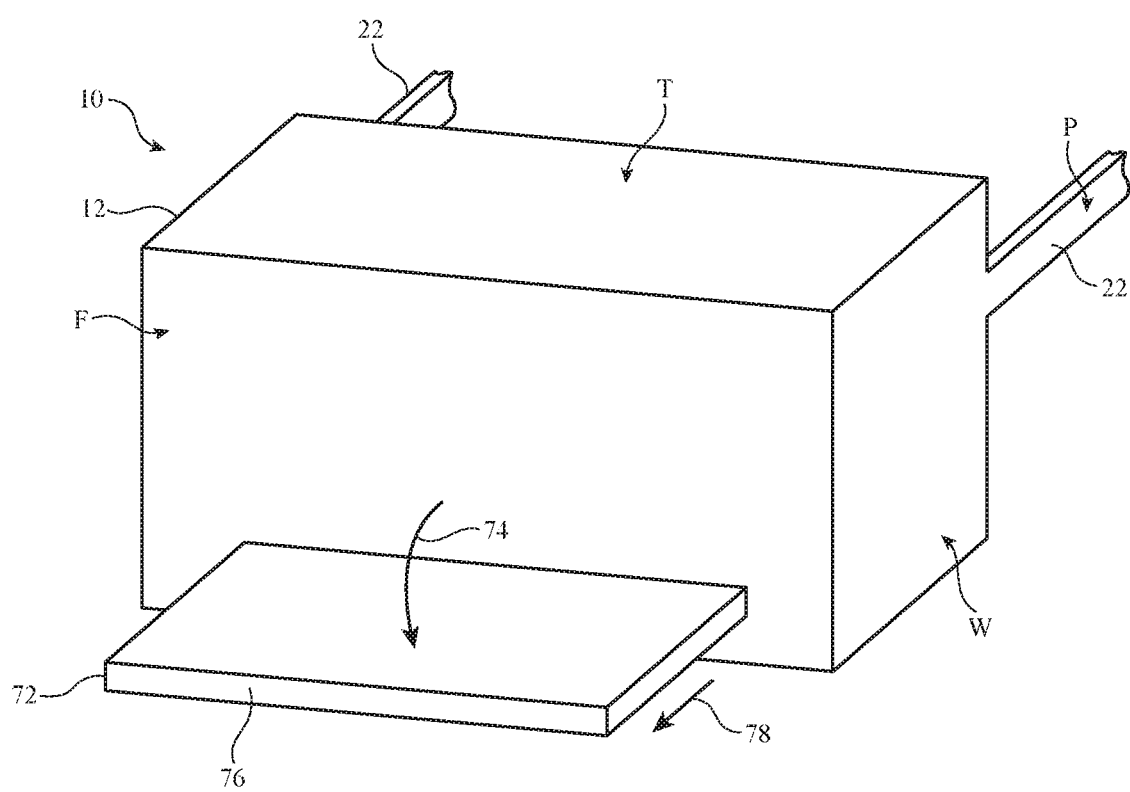
FIG. 7 is a front perspective view of an illustrative electronic device with a deployable input-output component on a movable member in accordance with an embodiment.

As shown in FIG. 7, device 10 may be provided with input-output components that can be stored when not in use. In the example of FIG. 7, member 72 can be stored on or in housing 12 when not in use. When it is desired to use member 72 to support interactions with device 10, member 72 may be folded downward in direction 74 (e.g., using a hinge coupled between member 72 and housing 12) or may be pulled out of a storage recess within device 10 in direction 78. Once deployed in this way, a user may supply input and/or receive output using member 72. As an example, input-output devices 42 (e.g., a touch screen display with selectable options forming keys for a keyboard, a physical keyboard, a track pad, buttons and/or touch sensors with haptic feedback, and/or other input-output devices 42) may be mounted on surface 76. When the input-output capabilities of these devices are not needed, member 72 may be stowed in device 10 (by folding or sliding member 72 into a desired storage location). When the input-output capabilities of these devices are desired, member 72 may be deployed by moving member 72 to a location that is convenient for the user, as shown in FIG. 7.

Figure 8:
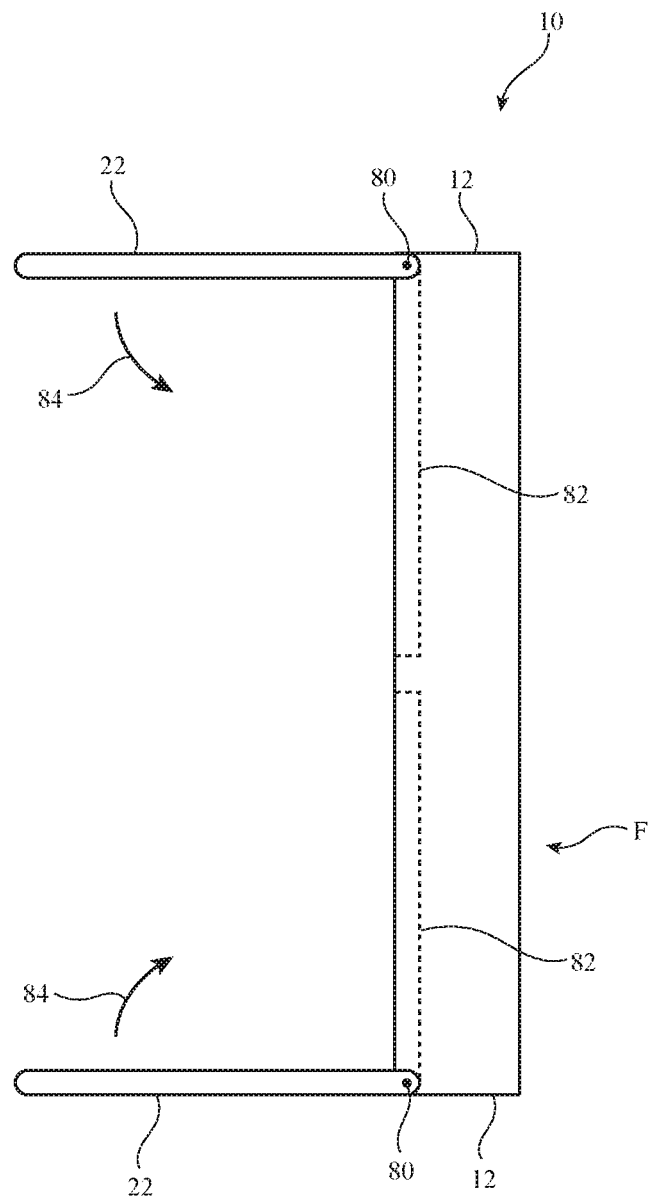
FIG. 8 is a top view of an illustrative electronic device with foldable head-mounted support structures in accordance with an embodiment.

If desired, electronic device 10 can be used as a stand-alone cellular telephone or other handheld portable device when not being used as a head-mounted device. Consider, as an example, illustrative electronic device 10 of FIG. 8. A shown in FIG. 8, device 10 may have head-mounted support structures 22 (e.g., eyeglass temples or other elongated head-mounted support structures) that are coupled to housing 12 using hinges 80. When it is desired to wear device 10 on the user's head, support structures 22 may be rotated away from housing 12 into the position shown in FIG. 8 or other suitable deployed position. When it is desired to stow structures 22 (e.g., when device 10 is not being worn on a user's head, support structures 22 may be rotated about hinges 80 in directions 84). This rotates structures 22 onto and/or into housing 12 for storage, as illustrated by storage locations 82 of FIG. 8.

Magnetic structures (e.g., magnets and/or magnetic material) may be provided on mating portions of support structures 22 and housing 12 and/or other mechanisms may be used to help retain support structures 22 in place against housing 12 during storage. Outer display 44 may be mounted on front side F or other external surface of device 10 for viewing when device 10 is not being worn on a user's head. This display may, for example, cover a rectangular front surface of housing 12. An inner display may face way from front side F for viewing while support structures 22 are deployed. Configurations in which a single display serves both as a touch screen for external output when device 10 is not being worn and as a display for presenting images to eye boxes 20 when device 10 is being worn may also be used.

As described above, one aspect of the present technology is the gathering and use of information such as sensor information. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

The foregoing is merely illustrative and various modifications can be made to the described embodiments. The foregoing embodiments may be implemented individually or in any combination.

What is claimed is:

1. An electronic device, comprising:
 a housing;
 head-mounted support structures coupled to the housing;
 a lens;
 a first display in the housing that is configured to present an image to an eye box through the lens;
 a non-removable second display that faces away from the first display and that is located on an external surface of the housing, wherein the non-removable second display is configured to display keyboard keys on the head-mounted support structures; and
 control circuitry configured to receive user input on the keyboard keys and display content on the non-removable second display when the first display is not presenting images and while the head-mounted support structures are not being worn, wherein the control circuitry adjusts the content on the non-removable second display based on the user input on the keyboard keys, and wherein the non-removable second display is movable between a deployed position and a stowed position.

2. The electronic device defined in claim 1 wherein the non-removable second display comprises a sensor selected from the group consisting of: a touch sensor that overlaps an array of pixels and a force sensor, wherein the control circuitry comprises wireless communications circuitry that is configured to communicate with external electronic equipment, and wherein the control circuitry is configured to gather input for the external electronic equipment using the sensor.

3. The electronic device defined in claim 1 wherein the electronic device comprises a projector display that is configured to project visual content onto a surface.

4. The electronic device defined in claim 1 further comprising a movable member that is coupled to the housing and is configured to move relative to the housing, wherein the electronic device comprises an electrical component on the movable member that is configured to gather additional user input.

5. The electronic device defined in claim 4 wherein the electrical component comprises a keyboard.

6. The electronic device defined in claim 4 wherein the electrical component comprises a touch screen display.

7. The electronic device defined in claim 1 wherein the non-removable second display comprises a touch sensitive display, the electronic device further comprising a proximity sensor configured to gather air gesture input.

8. The electronic device defined in claim 1 wherein the first display comprises an inner display, wherein the non-removable second display comprises an outer display, and wherein the control circuitry is configured to use the inner display to display the image while using the outer display to display the content.

9. The electronic device defined in claim 8 wherein the control circuitry is configured to display a given image simultaneously on the first display and the non-removable second display.

10. The electronic device defined in claim 8 wherein the content displayed on the non-removable second display is associated with the image displayed on the first display.

11. The electronic device defined in claim 1 wherein the user input on the keyboard keys is used to control an external electronic device while the head-mounted support structures are not being worn.

12. A method for operating an electronic device having a housing, head-mounted support structures coupled to the housing, a lens, a first display in the housing that is configured to present an image to an eye box through the lens, a second display on an external surface of the housing, and control circuitry, the method comprising:

with the second display, displaying content;

with the control circuitry, receiving user input on the second display while the first display is not presenting images and while the head-mounted support structures are not being worn; and with the control circuitry, adjusting the content on the second display based on the user input on the second display.

* * * * *